US008679139B2

(12) United States Patent
Aguirre et al.

(10) Patent No.: US 8,679,139 B2
(45) Date of Patent: Mar. 25, 2014

(54) DELIVERY SYSTEM FOR MAGNETIC ANASTOMOSIS DEVICE

(75) Inventors: Andres F. Aguirre, Chicago, IL (US); Brian K. Rucker, Winston-Salem, NC (US); Kevin Chmura, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 132 days.

(21) Appl. No.: 13/156,890

(22) Filed: Jun. 9, 2011

(65) Prior Publication Data

US 2012/0035628 A1    Feb. 9, 2012

Related U.S. Application Data

(63) Continuation-in-part of application No. 12/753,583, filed on Apr. 2, 2010.

(60) Provisional application No. 61/166,453, filed on Apr. 3, 2009.

(51) Int. Cl.
*A61B 17/08*    (2006.01)

(52) U.S. Cl.
USPC .......................................... 606/153

(58) Field of Classification Search
USPC ............... 606/10, 153, 151; 623/23.64
See application file for complete search history.

(56) References Cited

U.S. PATENT DOCUMENTS

| | | | |
|---|---|---|---|
| 5,690,656 A * | 11/1997 | Cope et al. ................... 606/153 |
| 6,273,917 B1 | 8/2001 | Inoue | |
| 6,802,847 B1 | 10/2004 | Carson et al. | |
| 6,932,827 B2 | 8/2005 | Cole | |
| 2003/0191497 A1* | 10/2003 | Cope ............................ 606/215 |
| 2004/0107004 A1 | 6/2004 | Levine et al. | |
| 2005/0070821 A1* | 3/2005 | Deal et al. ..................... 600/585 |
| 2005/0080439 A1 | 4/2005 | Carson et al. | |
| 2005/0182429 A1* | 8/2005 | Yamanouchi ................. 606/153 |
| 2005/0228412 A1 | 10/2005 | Surti | |
| 2006/0276825 A1* | 12/2006 | Mitelberg et al. ............. 606/200 |
| 2008/0114384 A1 | 5/2008 | Chang et al. | |
| 2009/0125042 A1 | 5/2009 | Mouw | |
| 2012/0035628 A1 | 2/2012 | Aguirre et al. | |

FOREIGN PATENT DOCUMENTS

WO    WO 2008/061024 A2    5/2008
WO    WO 2010/115116 A1    10/2010

OTHER PUBLICATIONS

U.S. Office Action dated Jul. 11, 2012 in related application.
International Search Report and Written Opinion (PCT/US10/029801).
International IPRP (PCT/US10/029801).
International Search Report/Written Opinion for PCT/US2010/061083 dated Apr. 21, 2011.
IPRP for PCT/US2010/061083 dated Jul. 4, 2012.

\* cited by examiner

*Primary Examiner* — S. Thomas Hughes
*Assistant Examiner* — Tin Nguyen
(74) *Attorney, Agent, or Firm* — Brinks Gilson & Lione

(57) ABSTRACT

A magnet delivery system for forming an anastomosis that comprises a wire guide; a catheter having a delivery portion for advancement into a intracorporeal space, the delivery portion having a lumen extending at least partially therethrough, and a strand connected to the catheter, whereby the magnet is disposed over the wire guide and distal to the catheter, and retained by the strand being releasably connected to the wire guide.

19 Claims, 12 Drawing Sheets

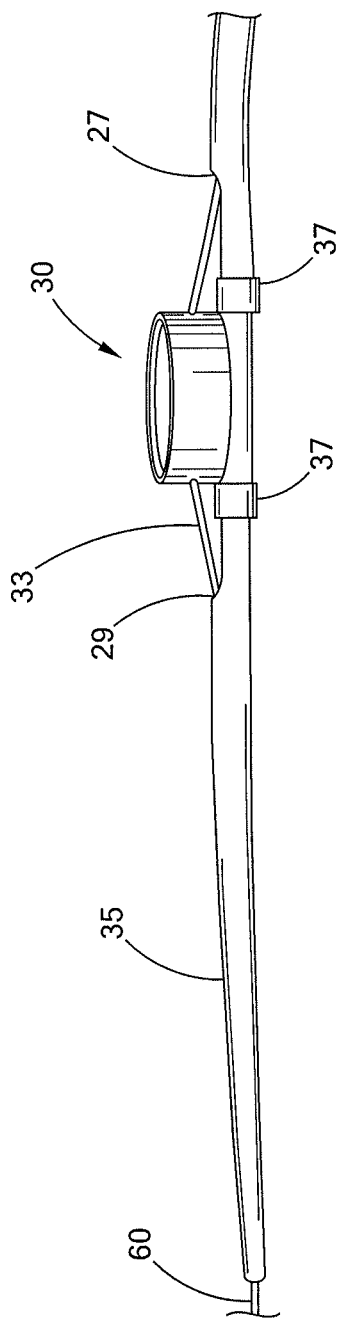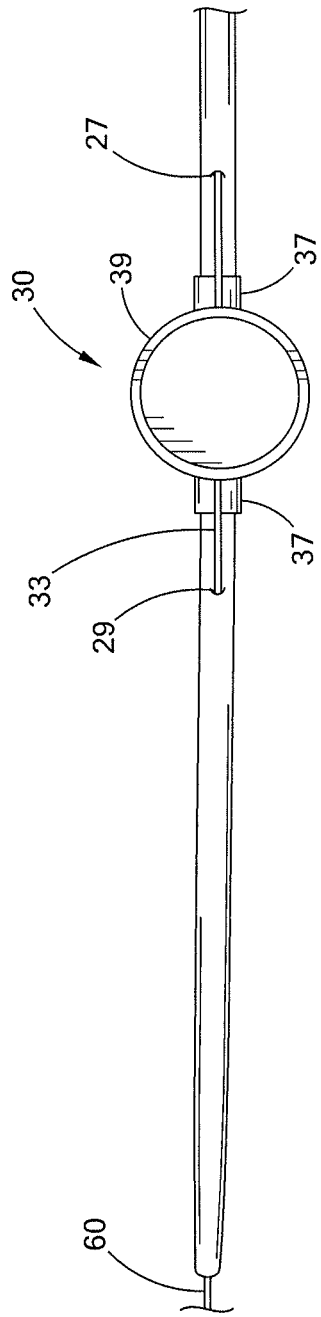

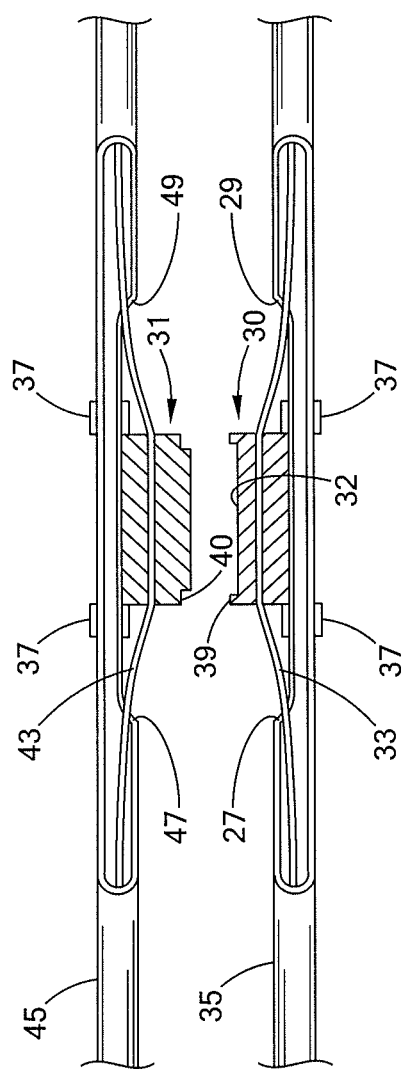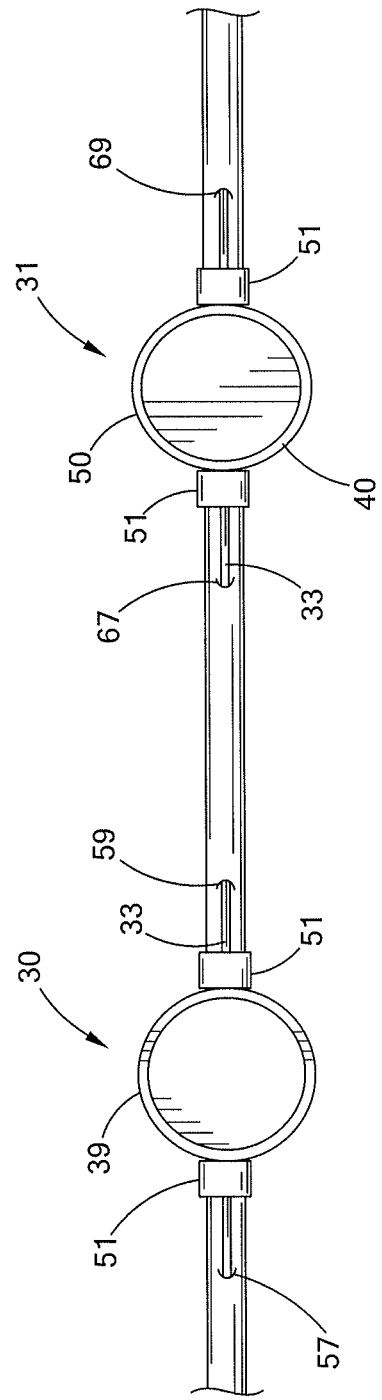

DELIVERY SYSTEM FOR MAGNETIC ANASTOMOSIS DEVICE

CROSS-REFERENCE TO RELATED APPLICATIONS

This application is a continuation-in-part of U.S. patent application Ser. No. 12/753,583 filed on Apr. 2, 2010, which claims the benefit of U.S. Provisional Application Ser. No. 61/166,453 filed on Apr. 3, 2009, entitled "DELIVERY SYSTEM FOR MAGNETIC ANASTOMOSIS DEVICE," the entire contents of which are incorporated herein by reference.

FIELD OF THE INVENTION

The present invention relates to delivery devices useful in delivering magnetic anastomosis devices.

BACKGROUND OF THE INVENTION

Magnetic anastomosis devices (MADs) are currently used to create a channel between two viscera for the purpose of redirecting bodily fluids. For example, intestinal contents or bile may be redirected in patients who have developed an obstruction of the bowel or bile duct due to such conditions as tumor, ulcer, inflammatory strictures, or trauma. A magnetic anastomosis device is disclosed in U.S. Pat. No. 5,690,656, the disclosure of which is incorporated herein by reference in its entirety. Generally, the MAD includes first and second magnet assemblies comprising magnetic cores that are surrounded by thin metal rims. Due to the magnetic attraction between the two magnetic cores, the walls of two adjacent viscera may be sandwiched and compressed between the magnet assemblies, resulting in ischemic necrosis of the walls to produce an anastamosis between the two viscera. The viscera treated by MADs include the gall bladder, the common bile duct, the stomach, the duodenum, and the jejunum of the small intestine.

Historically, MADs have been delivered through surgical intervention such as laparotomy, which of course is invasive and carries its own risks. The exemplary self-centering MAD of U.S. Pat. No. 5,690,656 permits delivery of the device over a wire guide and through the oral cavity, and typically under fluoroscopy. Alternatively, delivery can be accomplished by simply swallowing the magnet assemblies of the MAD and using massage under fluoroscopy to center the two magnet assemblies. Finally, delivery of the magnet assemblies has occasionally been performed endoscopically with grasping forceps, which can be time consuming and difficult. Removal of the MAD is typically accomplished by allowing the magnet assemblies to pass through the gastrointestinal track naturally, or more typically, with a follow-up endoscopic procedure using grasping forceps. Unfortunately, the relatively large size of the magnet assemblies can make delivery and retrieval complicated. In fact, balloon dilation of bodily lumens is often required in order to deliver the magnet assemblies to the desired location. Likewise, the size of bodily lumens is often the limiting factor in the size of the magnet assemblies that can be delivered and deployed.

Certain MAD procedures utilizing a jejunal magnet require the magnet to be passed down the esophagus to the stomach, and then through the pylorus and into the jejunum. Because of the curved nature of the passages leading to the jejunum, the magnet often becomes dislodged from the delivery system during advancement and placement thereof. Passing the jejunal magnet through the pylorus may be further complicated by patients with gastric outlet obstruction.

BRIEF SUMMARY OF THE INVENTION

Herein provided is a magnet delivery system for forming an anastomosis in a visceral space. The delivery system comprises a wire guide, a catheter, a strand and a first magnet. The catheter includes a delivery portion for advancement into a visceral space, the delivery portion having a first catheter lumen extending at least partially therethrough and slidably receiving the wire guide. The strand is connected to the catheter, and a distal end of the strand has a connector slidably connected to the wire guide. The connector is selectively detachable from the wire guide. The first magnet defines a lumen therethrough. The first magnet is detachably connected to the delivery portion of the catheter by disposing the first wire guide through the lumen of the first magnet such that a proximal end of the first magnet is positioned adjacent the distal end of the catheter, and disposing the strand alongside the first magnet and the connector of the strand to the wire guide at a location distal to the proximal end of the first magnet.

According to more detailed aspects, the connector includes an aperture sized to slidably receive the wire guide. The connector is preferably a loop formed by the strand, the loop defining the aperture. The loop may be formed by a distal end of the strand being folded over and connected to a distal portion of the strand, or may be formed by the strand being folded over and both ends of the strand extending proximally through the catheter. The connector is slidably attached to the wire guide at a point distal to the first magnet, whereby the first magnet is contained between the distal end of the catheter and the connector. In one embodiment, the first magnet defines an interior opening between its proximal and distal ends, the interior opening in communication with the lumen, and wherein the connector is slidably attached to the wire guide at a point within the interior opening. In some embodiments the strand is slidably connected to the catheter, while in others it is fixed. When slidably connected, the delivery potion of the catheter preferably includes a second catheter lumen extending at least partially therethrough, the second catheter lumen slidably receiving the strand. When fixedly connected, the strand is also preferably fixedly attached to the connector, which may comprise a short tube separately formed from the strand.

According to still further detailed aspects, the system is operable between a delivery configuration and a deployed configuration while the first magnet is in vivo, the delivery configuration including the wire guide positioned within the lumen of the first magnet such that a proximal end of the first magnet is positioned adjacent the distal end of the catheter, and the strand extending alongside the first magnet and the connector slidably attached to the wire guide at a location distal to the proximal end of the first magnet, the deployed configuration including the connector being detached from the wire guide and the wire guide removed from the lumen of the first magnet. A suture lock may be positioned at a proximal end of the catheter, the suture lock operable to fix the position of the strand portions extending through the suture lock relative to the catheter. Here, a proximal portion of the catheter preferably includes a side opening, and wherein the wire guide extends through the side opening and does not extend through the suture lock.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 1 is a perspective view of the delivery system constructed in accordance with the teachings of the present invention;

FIG. 2 is an overhead view of the delivery system;

FIG. 3 is a perspective view of two delivery systems with complementary jejunal magnets;

FIG. 4 is an overhead view of a dual delivery system;

DETAILED DESCRIPTION OF THE INVENTION

Figure 5:
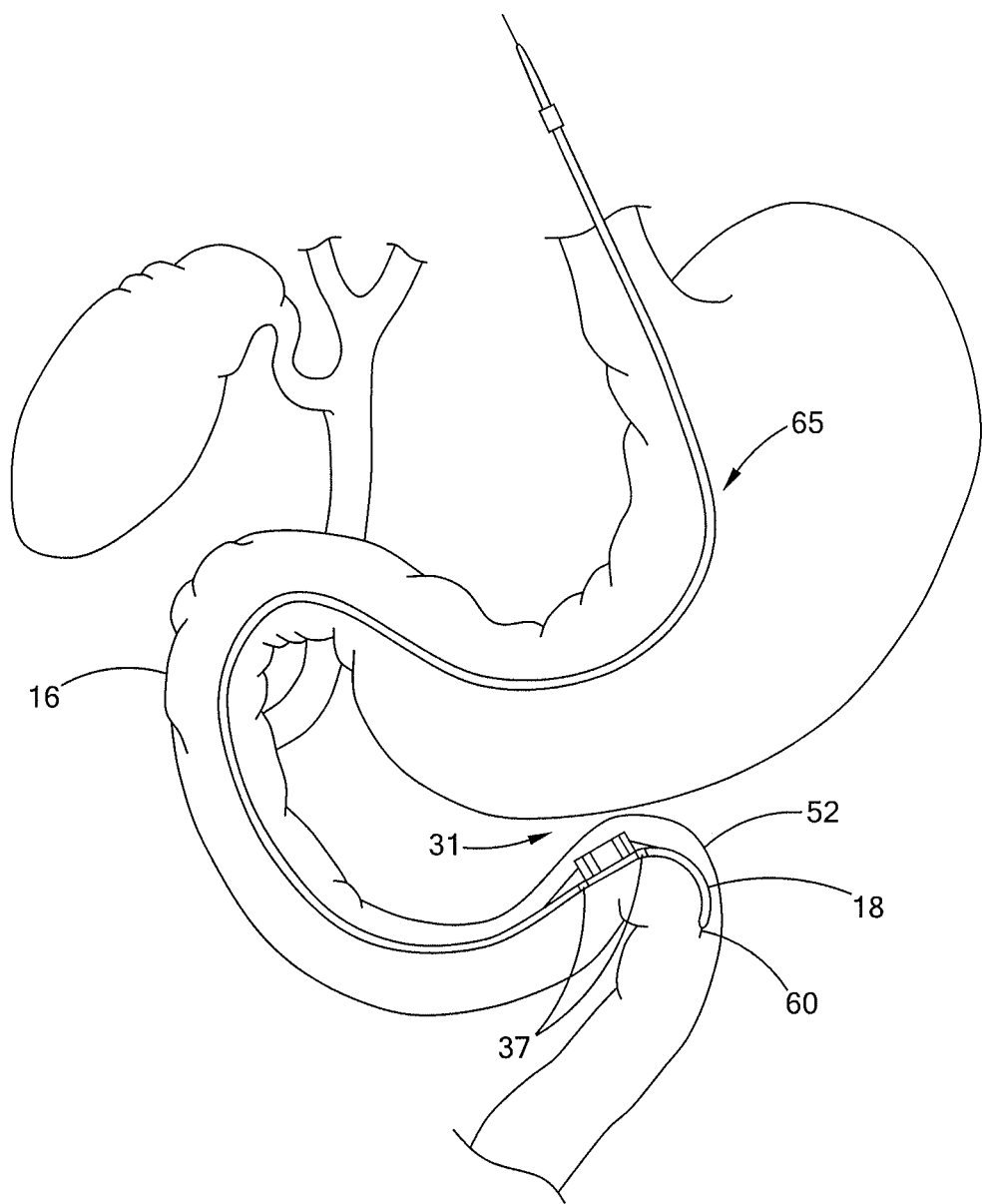
FIGS. 5, 6, and 7 schematically depict the use of two magnet assemblies for forming a magnetic anastamosis device in accordance with the present description.

The term "prosthesis" means any replacement for a body part or for a function of that body part or any device that enhances or adds functionality to a physiological system.

The term "catheter" generally means a medical device comprising an elongate shaft having a lumen extending at least partially therethrough, including balloon catheters, guide catheters, delivery catheters, sheaths and cannulas. An example of a catheter includes the Cook Medical Fusion™ Biliary Dilation Catheter (FS-BDC).

The magnet delivery system uses a catheter 35 and a wire guide 33 to deliver a jejunal magnet 30. As seen in FIG. 1, the catheter 35 has two ports, a first port 27 and a second port 29 in communication with the lumen of the catheter and through which the wire guide 33 is placed. Suitable wire guides can include the Cook Medical Tracer Hybrid® Wire Guides (HYB-48015). The proximal 27 and distal 29 ports are sufficiently spaced apart to accommodate the magnet 30 between them. The ports 27, 29 are about 35 mm to about 70 mm apart or any combination or subcombination of ranges therein. In the particular embodiment illustrated, the ports 27, 29 can be spaced about 60 mm apart. The first and second ports 27, 29 are formed through the catheter 35 wall and are spaced proximally from the distal end of the catheter 35 so as to be distinguished from the entry or exit openings of the catheter at the very proximal or distal ends thereof. The ports 27, 29 are preferably longitudinally aligned. The preferred distance between the ports will depend on the diameter and size of the magnets. Magnet sizes will range across standard sizes used in the field. These ports 27, 29 are located in the distal part of the catheter 35 and are appropriately spaced to accommodate magnets of various sizes in diameter. Magnets between about 10 mm and 20 mm in diameter or any combination or subcombination of ranges therein may be accommodated, although a magnet about 14 mm in diameter is illustrated. For other magnet sizes the location of the ports in the wire guide lumen may be modified as required.

The magnet 30 shown has a general disc shape (i.e. having an axial height which is less than the outer diameter). Magnets that may be used in this delivery system can be circular, cubular, cylindrical, polygonal, oval or ovoid, square, or the like. Numerous other shapes of the magnets may be readily envisioned by those skilled in the art. For example, referring to FIGS. 8a, 8b and 9, the magnet may include an elongate magnet as described in U.S. patent application Ser. No. 12/971,906, filed Dec. 17, 2010, entitled "Elongate Magnet for a Magnetic Anastomosis Device," the entire contents of which are incorporated herein by reference. The magnet 30 may include a protective coating which may be formed of various materials such as polymers like Teflon® or Paralene® for protection of the magnetic core from the corrosive effects of digestive acids or other bodily fluids depending upon the bodily structure involved.

The magnet 30 has a lumen therethrough to accommodate the wire guide 33. The magnet 30 also comprises an annular edge 39 along the magnet's perimeter. The edge 39 is slightly raised above the center of the magnet 30 such that it forms a basin 32 to accommodate or mate with a second magnet (as described below). In particular, when the magnet 30 is delivered, this edge 39 contacts the wall of the viscera and helps to initiate the ischemic necrosis of the tissue captured between the magnet 30 and a mated second magnet. A radiopaque marker 37 is placed on the catheter in the vicinity of the magnet to mark the magnet location when viewed through fluoroscopy. A radiopaque marker can be placed underneath the magnet 30 on the catheter 35 to mark the location of the magnet when viewing the delivery system from the side.

The wire guide 33 holds the magnet 30 in place on the distal end of the catheter 35. In FIGS. 1 and 2, the wire guide 33 is shown protruding from the first port 27, going through the lumen of the magnet 30, and re-entering the catheter 35 at the second port 29. The catheter 35 may include radiopaque markers 37 that permit tracking of the delivery system for accurate positioning of the magnet 30. It may be preferred that a radiopaque marker 37 be placed immediately distal to the magnet 30. The catheter 35 may be used alone or in conjunction with other wire guide cannulae for navigation of the bodily lumens and delivery of a magnet.

Figure 7:
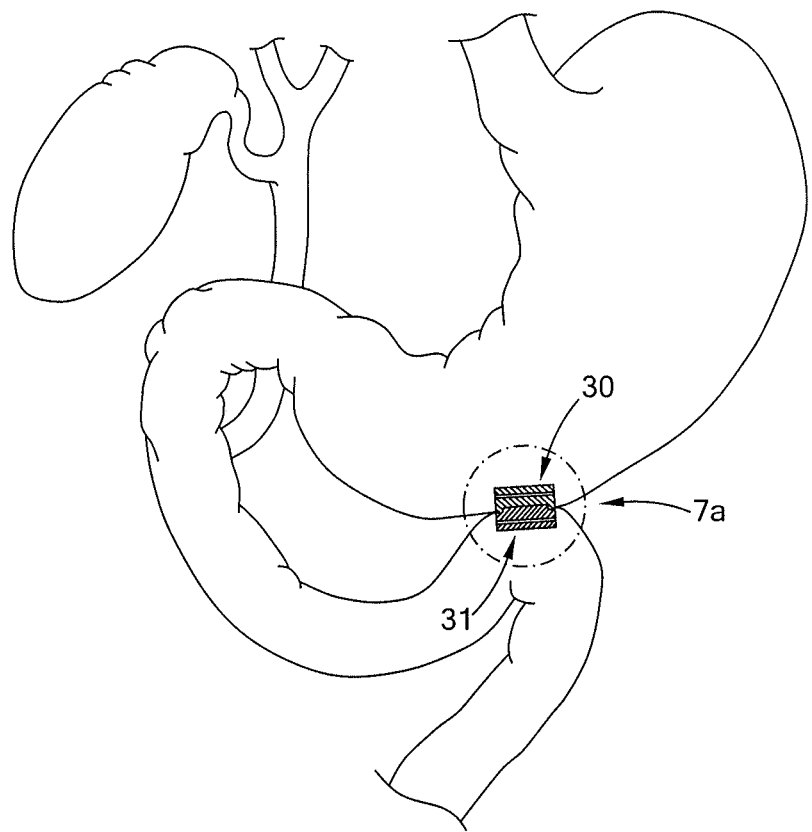
Figure 7A:
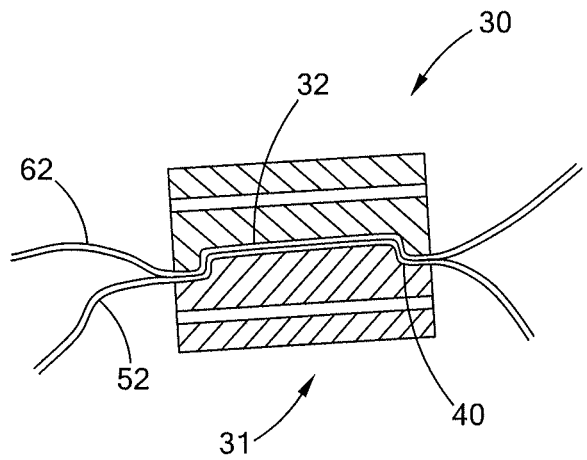
FIG. 7a is a cross-sectional view of two magnets compressing the walls of two internal bodily organs to facilitate a new anastamosis.

FIG. 3 shows two delivery systems where a second magnet 31 is affixed to a second catheter 45 having a second wire guide 43 passing through a first port 47, the second magnet 31, and a second port 49. The second magnet 31 has an annular recess 40 that is capable of mating with the annular edge 39 of the first magnet 30. FIG. 7a shows the walls 52, 62 of two viscera being compressed between magnets 30, 31. The edge 39 compresses the walls against the second magnet 31 to assist the ischemic necrosis. The second magnet 31 can also have an annular edge with a smaller diameter than the first magnet 30. When implanted and mated with the first magnet 30, the second magnet 31 can fit within the annular edge 39 of the first magnet 30.

FIG. 4 shows a system for the delivery of two magnets 30, 31. Such a system may be used as an efficient means of delivering multiple magnets. Although two magnets 30, 31 are shown, more than two magnets can be coupled to a catheter in the fashion described herein. The catheter has four holes in total: first 57 and second 67 proximal ports and first 59 and second 69 distal ports. First magnet 30 is held between first port 57 and second port 59 with wire guide 33. The second magnet 31 is constrained between first port 67 and second port 69 with wire guide 33. The first magnet 30 comprises an annular edge 39 with a basin 32. The annular recess 40 on the second magnet 31 mates with the annular edge 39 of the first magnet 30 when both magnets 30, 31 are implanted. Two sets of radiopaque markers 51 can be used with a second radiopaque marker located distal to the second magnet 31. In general, the radiopaque markers can be located on the delivery portion sufficient to guide an operator during the placement procedure. Methods for delivering both magnets using such a system are described further below.

It will be recognized by those skilled in the art that the magnetic anastomosis device employing the magnet assemblies described herein not only preserves the benefits of improving the time of the procedure to place the magnet, but further provides a small delivery configuration which may be easily located within the body for accurate delivery. The delivery systems described herein also provide for insertion of the magnets through natural orifices. As such, there is also a method for delivering the magnet assembly to a position for forming an anastamosis between two viscera. FIG. 5 shows the relative positions of several viscera in the abdominal cavity, including the gall bladder 10, the common bile duct 12, the stomach 14, the duodenum 16, and the jejunum 18 of the small intestine. Although not shown, the delivery system described herein may also be used to implant anastomosis-forming magnets in the colon for possible use in gastric bypass procedures. The delivery system described herein can be used, for example, to create an anastomosis between the stomach 14 and the jejunum 18 of the small intestine. The delivery system can also be used as a part of procedure where forceps are used to place one of the magnets.

The method for delivering a jejunal magnet to form an anastamosis comprises introducing the delivery system 65 into an endoluminal vessel. FIG. 5 shows the system 65 being advanced to the jejunum 18. The delivery of magnet 31 follows once the wire guide 60 has been positioned adjacent the wall of a first viscus. In FIG. 5, the first viscus is the jejunum 18. The magnet 31 is placed on catheter 35 as shown in FIG. 1 and held in place on the catheter 35 by the wire guide 33. The wire guide 33 is loaded through the catheter 35, passing through second port 29 in the catheter 35 lumen, through the lumen of the magnet 30, and then reentering the catheter 35 lumen through first port 27. Using the radiopaque markers 37 as a guide, the catheter 35 is advanced such that the magnet 31 is placed adjacent to the wall of the jejunum 18 as shown in FIG. 6.

Figure 6:
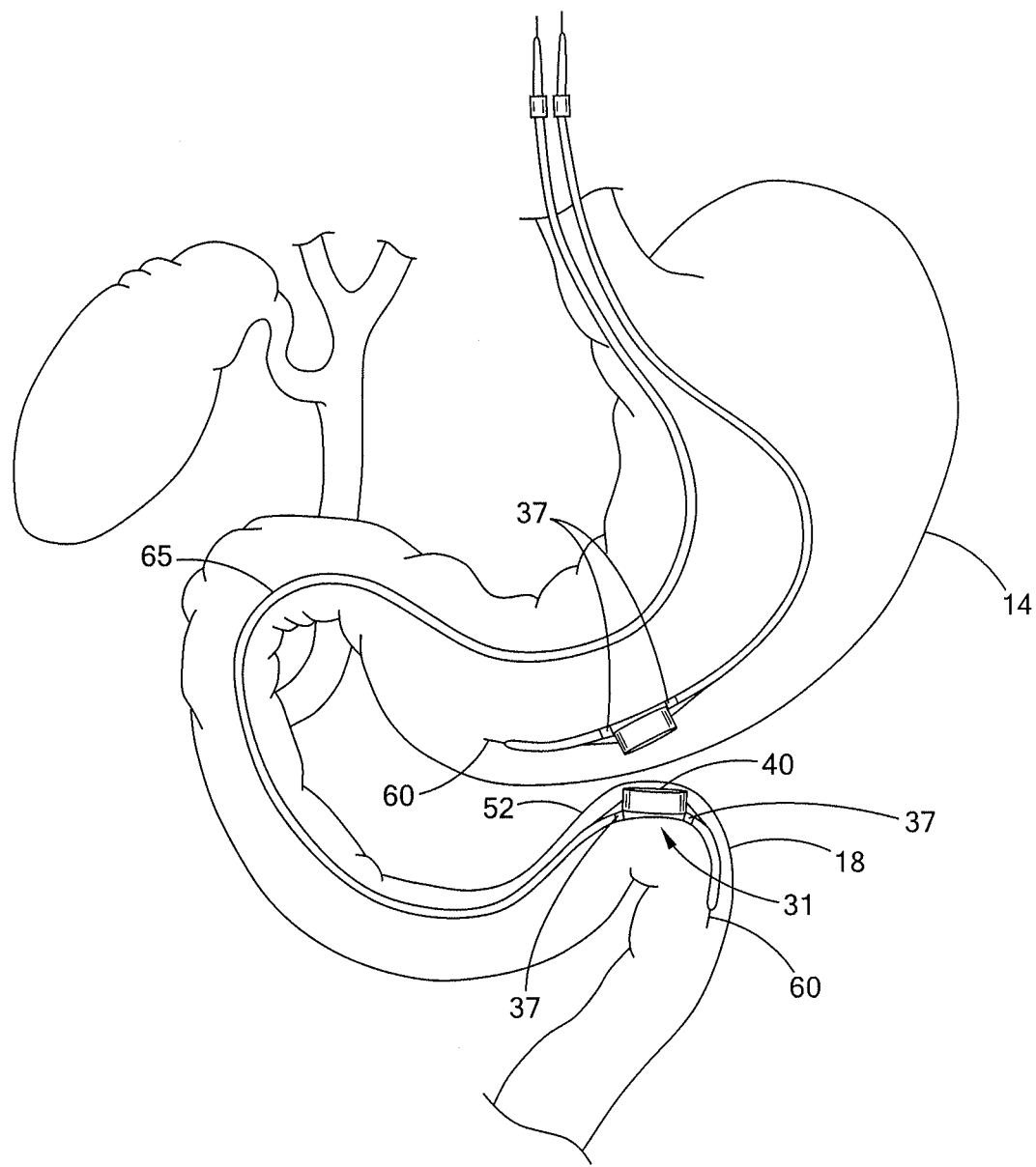

The delivery system 65 with magnet 31 remains in position as a second delivery system 70 is introduced into the stomach 14 as shown in FIG. 6. Magnet 30 is positioned adjacent the wall of the stomach 14 that borders the jejunum 18 near the location of magnet 31. Magnets 30, 31 are released so that the magnetic forces attract the magnets together, compressing the walls 52, 62 together of the jejunum 18 and the stomach 14 as seen in FIG. 7. To release magnet 31, the operator removes the wire guide 33 and then the catheter 35.

The attraction forces exerted between the magnets 30, 31 is strong enough so that in the event that the catheter 35 is caught between the two magnets 30, 31 after the placement of magnet 30, the catheter 35 may be removed and the magnets 30, 31 will remain together. The radiopaque markers 37 can be used as a guide to help position the magnet 31 in the correct orientation under fluoroscopy. A radiopaque marker 37 may be located at the proximal edge of the magnet as exemplified in FIG. 1.

Once the necrosis of the walls of the stomach and the jejunum is complete, an anastomosis is formed. The magnets 30, 31 can then pass through the body naturally or can be removed by means such as laparotic removal, endoscopic removal, or other procedure.

The delivery system shown in FIG. 4 can be used to deliver two magnets using one catheter. Magnet 31 can be delivered first to a first location to be treated by retracting the guidewire 33 sufficiently to release the magnet 31. The delivery portion of the catheter can then be positioned in a second location where magnet 30 can be released by further retracting the guidewire 33 from the lumen of the magnet 30. The magnets 30, 31 can be maneuvered to mate with one another by massage under fluoroscopy or by grasping forceps through laparoscopic surgery. Once mated, the ischemic necrosis process can begin on the walls of the two viscera being treated.

Figure 8A:
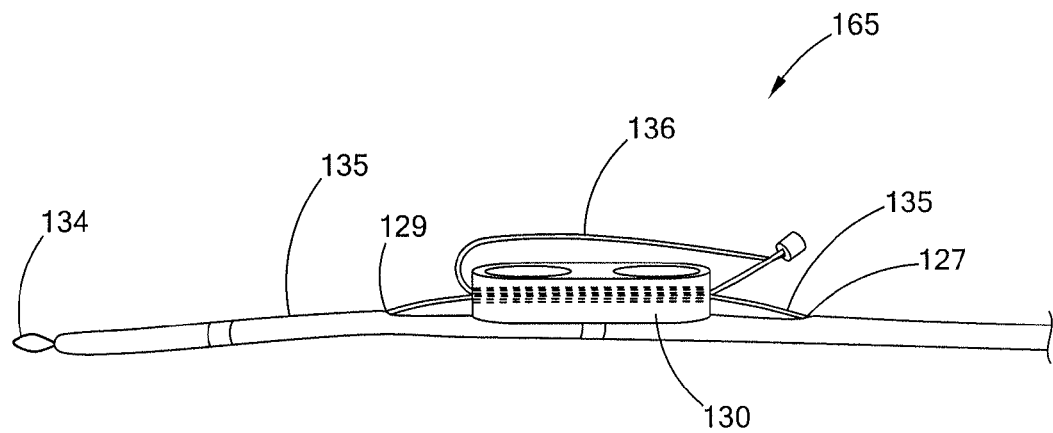
FIGS. 8a and 8b are perspective views of a delivery system for delivering a magnetic anastamosis device constructed in accordance with further teachings of the present description.
Figure 8B:
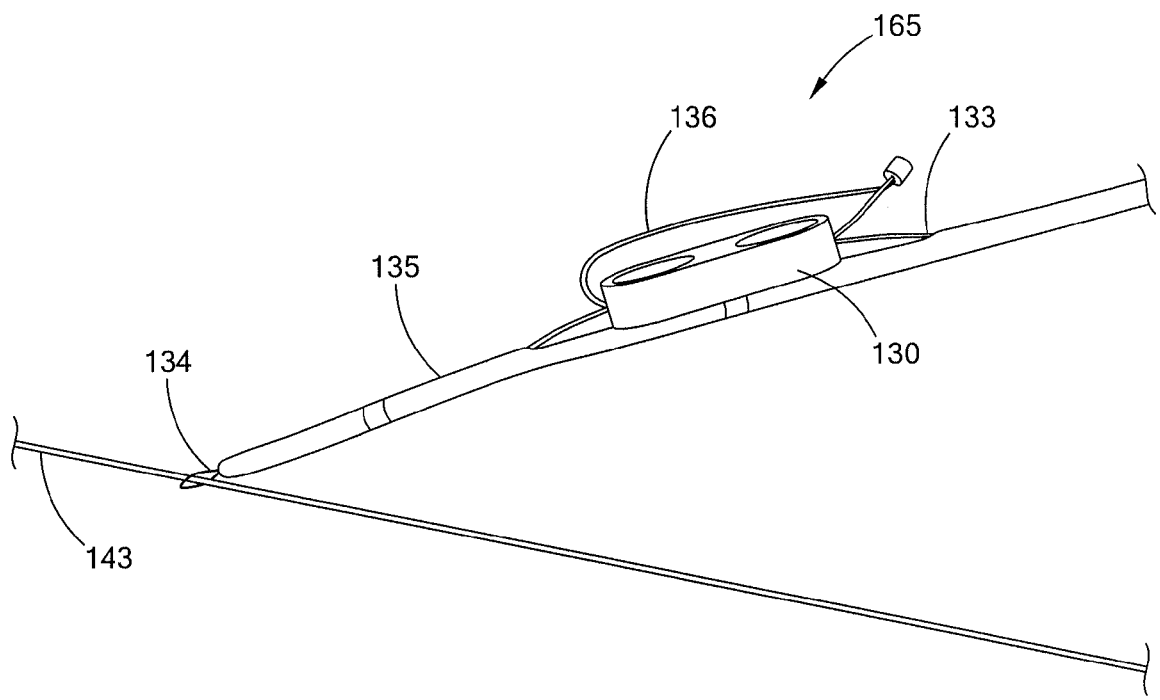

FIGS. 8a and 8b depict an alternative embodiment of a delivery system 165 in accordance with the teachings of the present description and having a description similar to that of FIG. 1, and in which similar components are denoted by similar reference numerals increased by 100. The delivery system 165 uses a catheter 135 with ports 127 and 129 and a wire guide 133 to deliver a magnet 130. In this embodiment, the wire guide 133 includes a loop 134 at a distal end thereof. The loop 134 extends beyond a distal end of the catheter 135.

As shown in FIG. 8b, the loop 134 slides over a second wire guide 143 during delivery of the magnet 130. For example, in one method of delivery, the wire guide 143 is positioned in the target site. The catheter 135 is then backloaded onto the wire guide 143 via the loop 134. In other words, the loop 134 slidably receives the wire guide 143 and the catheter 135 is pushed relative thereto until the target site is reached. The magnet 130 is then placed adjacent a bodily wall. Another magnet is delivered in the same fashion to another target site to mate with the magnet 130 to compress the bodily walls therebetween. Once the magnets mate, the wire guide 143 is removed followed by removal of the wire guide 133. Thereafter, the catheter 135 is removed.

In this embodiment, an elongate magnet 130, as described in U.S. Provisional Application No. 61/291,202, is shown. The elongate magnet 130 may or may not include the suture 136 shown extending through the lumen of the magnet 130 which may aid in positioning of the magnet 130. The delivery system 165 is advantageous for delivering larger, elongate magnets 130. The delivery systems described above may be used to deliver the elongate magnet 130. However, since the elongate magnet 130 is larger than the magnets 30, 31 disclosed in the earlier described embodiments, a greater force would be needed to advance the elongate magnet 130 over the wire guide 33 due to the larger area of friction between the elongate magnet 130 and the catheter 35. With the embodiment shown in FIGS. 8a and 8b, the extra force is eliminated as the magnet 130 moves with the catheter 135 as it slides along the external wire guide 143.

Figure 9:
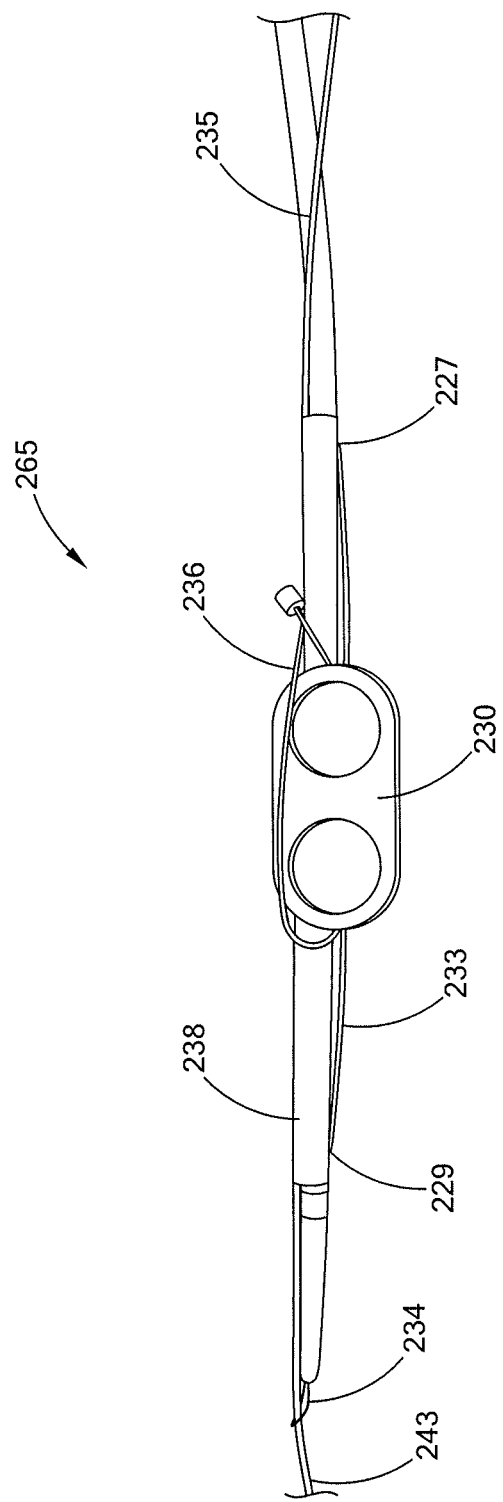
FIG. 9 is an overhead view of a delivery system for delivering a magnetic anastomosis device constructed in accordance with further teachings of the present description.

FIG. 9 depicts another embodiment of a delivery system 265 in accordance with the teachings of the present description and having a description similar to that of FIG. 1, and in which similar components are denoted by similar reference numerals increased by 200. The delivery system 265 uses a catheter 235 and a wire guide 233 to deliver a magnet 230. In this embodiment, the distal loop 234 of the wire guide 233 slidably receives a second wire guide 243, similar to FIGS. 8*a* and 8*b*, thus providing reduced force needed during delivery of the magnet 230. In this embodiment, however, a dual lumen outer sheath 238 slidably receives the catheter 235 in one lumen and the wire guide 233 in a second lumen. The outer sheath 238 includes ports 227 and 229. The magnet 230 again preferably includes a looped suture 236.

During delivery of the magnet 230 with the delivery system 265 of FIG. 9, a larger portion of the catheter 235 remains closer to the wire guide 243 rather than merely the distal end as is the case with the system 165 of FIGS. 8*a* and 8*b*. This improves the trackability of the catheter 235 and reduces the likelihood that the catheter will bow in the stomach.

Alternatively, instead of being housed within an outer sheath, the catheter 235 may include two lumens; one for the wire guide 233 to hold the magnet and the other for the main wire guide 243. The distal loop 234 slides over the main guide wire 243 during delivery of the magnet 230.

Figure 10:
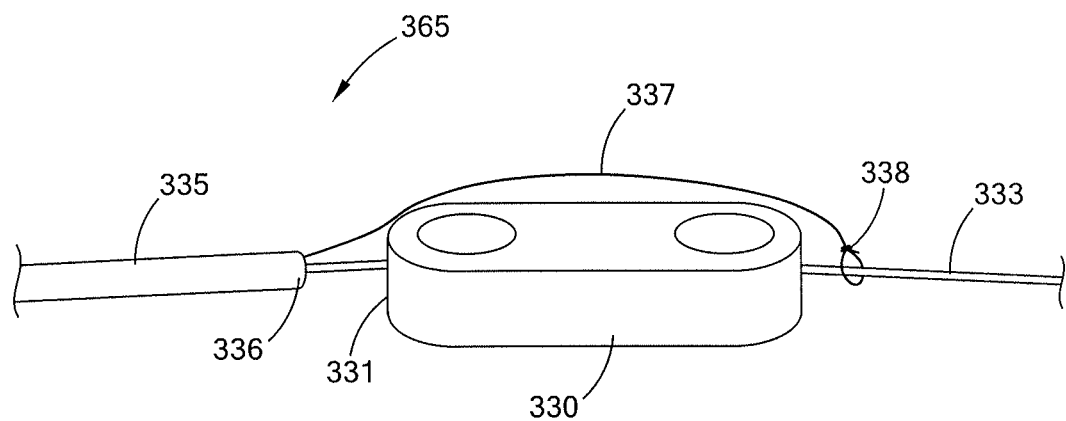
FIG. 10 is a perspective view of another embodiment of a delivery system constructed in accordance with the teachings of the present invention.
Figure 11:
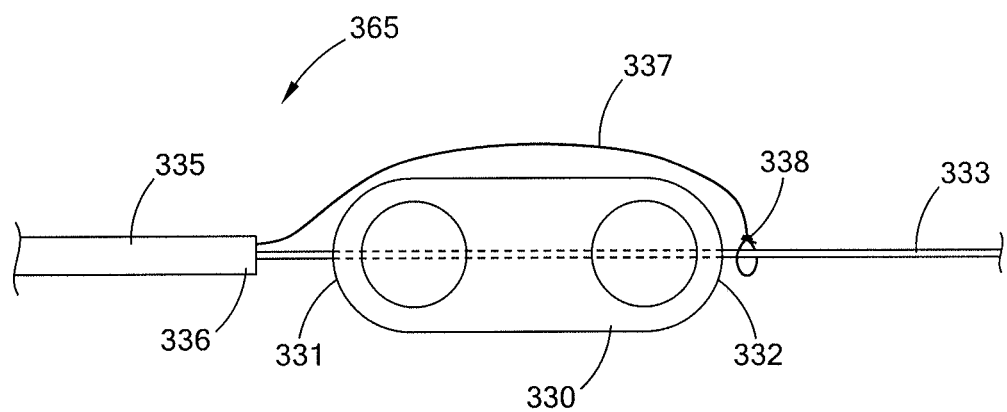
FIG. 11 is a top view of the delivery system depicted in FIG. 10.

Turning now to FIGS. 10-13, another embodiment of a magnet delivery system 365 is shown. As best seen in FIG. 10, the system 365 includes a catheter 335 having a distal end 336 from which both a wire guide 333 and a strand 337 project. The strand 337 is preferably constructed of suture or other string-like material suitable for use within the body. In this embodiment, rather than being mounted directly on the catheter 335, the magnet 330 is located distally beyond the catheter 335, and in particular the proximal end 331 of the magnet 330 is positioned distal to the distal end 336 of the catheter 335. It will be recognized the magnet's proximal end 331 may abut the distal end 336 of the catheter 335. The magnet 330 again includes an internal lumen 332 that slidably receives the wire guide 333. The strand 337 extends alongside and around the magnet 330, and is slidably attached to the wire guide 333 at a position distally beyond the proximal end 331 of the magnet 330, and preferably distally beyond the entire magnet 330 as shown. In the depicted embodiment, the distal end of the strand 337 is folded over and tied to itself to form a loop 338 which serves as a connector for slidably connecting the strand 337 to the wire guide.

Figure 12:
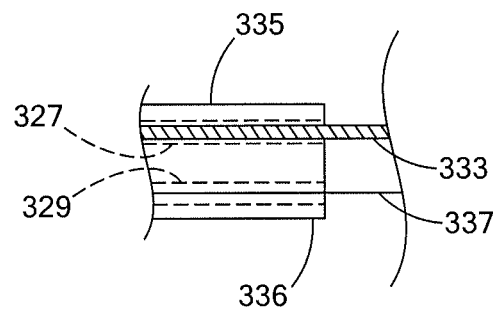
FIG. 12 is a cross-sectional view, partially cut-away, of the delivery system depicted in FIG. 10.
Figure 13:
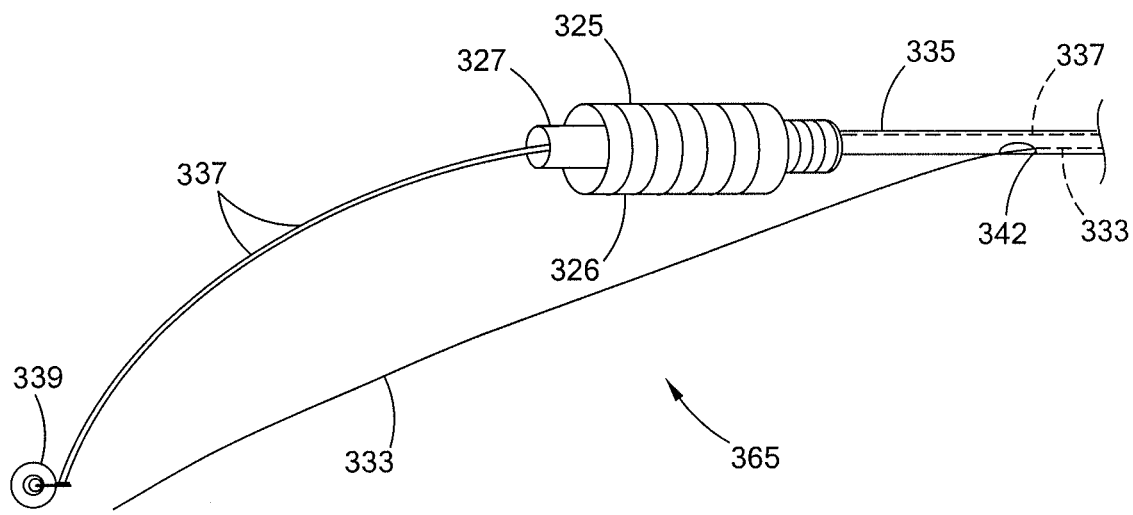
FIG. 13 is a perspective view of a proximal end of the delivery system depicted in FIG. 10.

As best seen in FIG. 12, the catheter 335 is preferably a dual lumen catheter, and includes a first lumen 327 and a second lumen 329 extending longitudinally through at least a portion of the catheter 335. In this manner, both the wire guide 333 and the strand 337 may move through the catheter 335 without interference with one another. As best seen in FIG. 13, the proximal end of the delivery system 365 is shown, wherein the catheter 335 is connected to a proximal end device 325. The proximal end device 325 may include various known structures such as handles, visualization instruments, control instruments or the like. In the depicted embodiment, the proximal end device 325 includes a suture lock which is generally known in the art, and includes an exterior component 326 and an interior component 327 which serve to grasp and lock the strand 337 relative to the catheter 335. A ring 339 or other enlarged object may be attached to the strand 337 at its proximal end so that it does not pass completely through the suture lock 325. Preferably, the proximal end of the catheter 335 also includes a side opening 342 which is formed as a skive, and opens to only the first lumen 327 (which carries the wire guide 333). In this manner, the strand 337 may be fixed by the suture lock 325, while the wire guide 333 is allowed to bypass the lock 325 and does not interfere with it or the strand 337.

Figure 18:
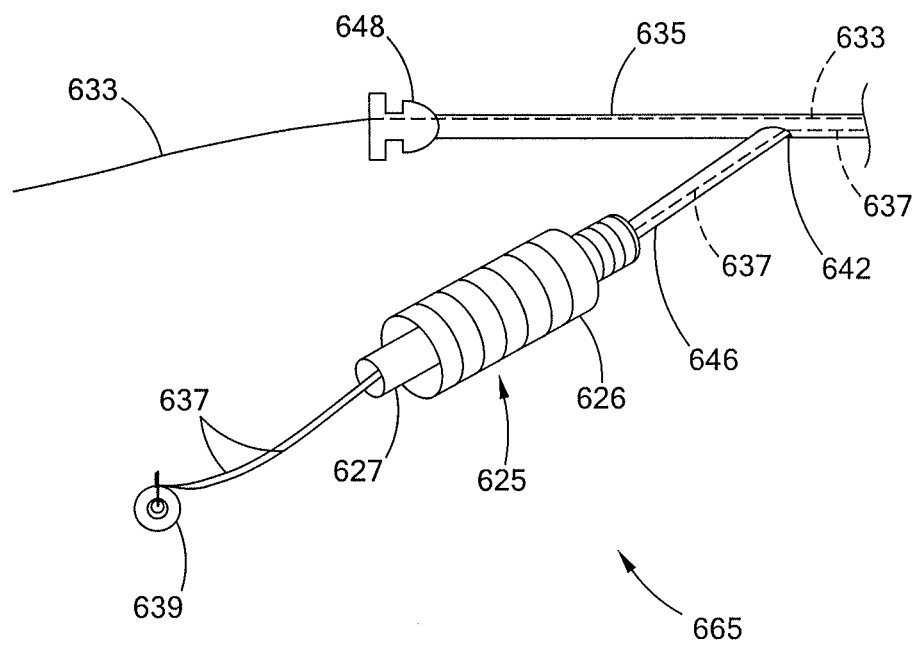
FIG. 18 is a perspective view of yet another embodiment of a proximal end of the delivery system depicted in FIG. 13.

In a variation of the embodiment shown in FIG. 13, the system 365*a* may further include a cannulated hub 344 in communication with the catheter 335 at the side opening 342. The cannulated hub 344 generally includes a short tubular member or cannula 346 having a hub 348 formed at the free, proximal, end thereof. This variation further supports the side opening 342, and the hub 348 may be designed to connect to various other catheter devices as desired. Similarly, in another variation of the system 665 shown in FIG. 18, the wire guide 633 may be designed to extend linearly through the distal end of the catheter 635, while the strand 637 extends through the side opening 642. Here, the proximal end of the catheter 635 is formed with a hub 648, while the suture lock 625 (having exterior component 626 and interior component 627) is communicated to the side opening 642 via cannula 646. A ring 639 is attached to the ends of the strand 637 as in the prior embodiment.

With reference back to FIGS. 10 and 11, it can be seen that the tension on the strand 337 can be used to hold the magnet 330 at the distal end 336 of the catheter 335, which in turn can be fixed using the suture lock 325. In this way, the lock 325, catheter 335 and strand 337 may all be slid relative to the wire guide 333 to position the magnet 330 as discussed above. To deploy the magnet 330, the wire guide 333 may be retracted proximally such that it passes through and is removed from the connector loop 338 of the strand 337, and from the lumen 332 of the magnet 330. In will be recognized that the wire guide 333 may be withdrawn so that its distal end only passes through the connector loop 338 of the strand 337, whereby the strand 337 no longer maintains the magnet 330 at the distal end 336 of the catheter 335. The magnet 330 may then be pushed off using the catheter 335, or the wire guide 333 may simply be retracted further proximally.

Figure 14:
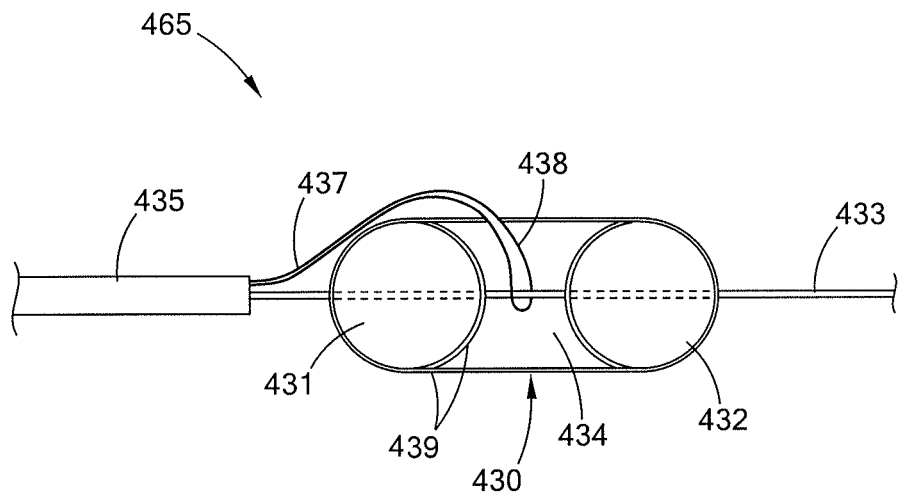
FIG. 14 is a top view of yet another embodiment of a delivery system constructed in accordance with the teachings of the present invention.

Turning now to FIG. 14, another embodiment of a magnet delivery system 465 is shown. As with the other embodiments, the system 465 includes a catheter 435 slidably receiving a wire guide 433 and a strand 437. It can be seen that the magnet 430 includes a frame 439 that supports the magnetic elements 431 and 432. The frame is thus an elongated oval shape with two interior circular portions for the individual magnetic elements 431, 432. The magnet 430 and its frame 433 define an interior space 434 between the magnetic elements 431, 432 that is in communication with the lumen of the magnet 430. Accordingly, the strand 437 is permitted to pass into the interior space 434 and be slidably attached to the wire guide 433 via its connector 438. Neither the strand 437 nor the connector 438 are directly attached to the magnet 430.

Figure 16:
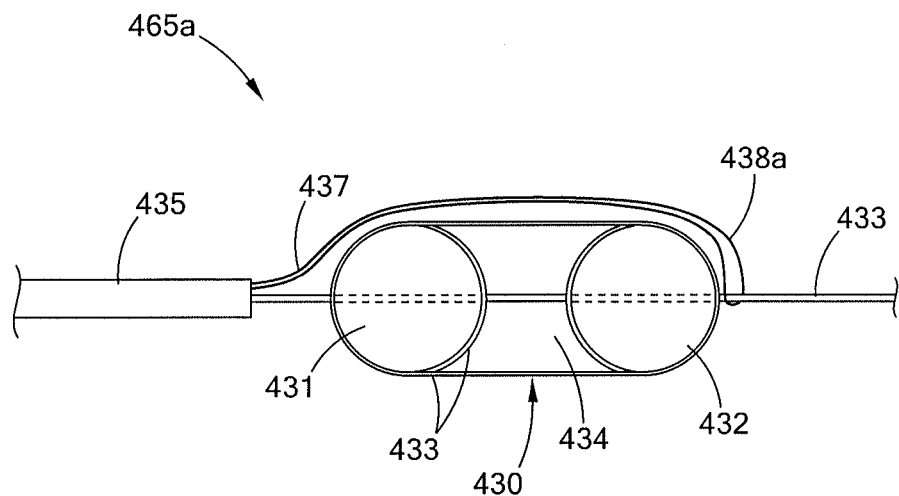
FIG. 16 is a top view of yet another embodiment of a delivery system constructed in accordance with the teachings of the present invention.
Figure 17:
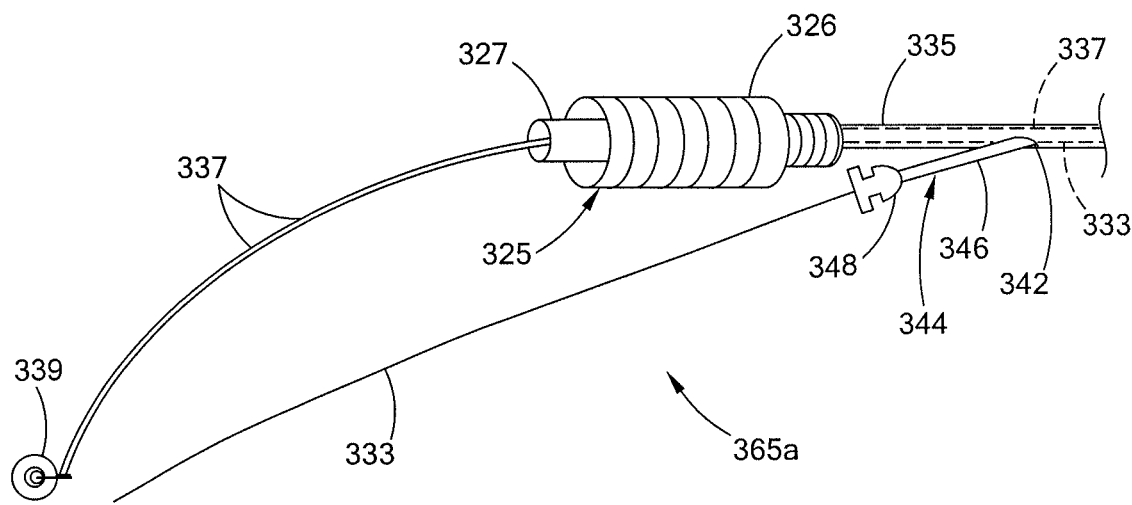
FIG. 17 is a perspective view of another embodiment of a proximal end of the delivery system depicted in FIG. 13.

In the depicted embodiment, the proximal end of the strand 437 is simply wrapped around, i.e folded over, the wire guide 433 within the interior space 434 and then extended back proximally through the same lumen of the catheter 435, leaving a loop 438 around the wire guide 433. The strand preferably extends completely to the proximal end of the system 465, such that both ends of the strand 437 are accessible and operable to the operator. In this way, the wire guide 433 does not need to be withdrawn proximally to detach it from the loop connector 438 formed by the strand 437, but rather one end of the strand 437 may be pulled from the proximal end of the system 465 to remove the loop 438 formed around the wire guide 433. As with the prior embodiments, when the wire guide 433 is completely withdrawn from the lumen of the magnet 430 the magnet 430 is deployed. It will also be recognized that, in a variation of the system 465*a*, the strand 437 may be wrapped around the wire guide 433 to form a loop 438*a* at a location distal to the magnet 430, as shown in FIG. 16.

Figure 15:
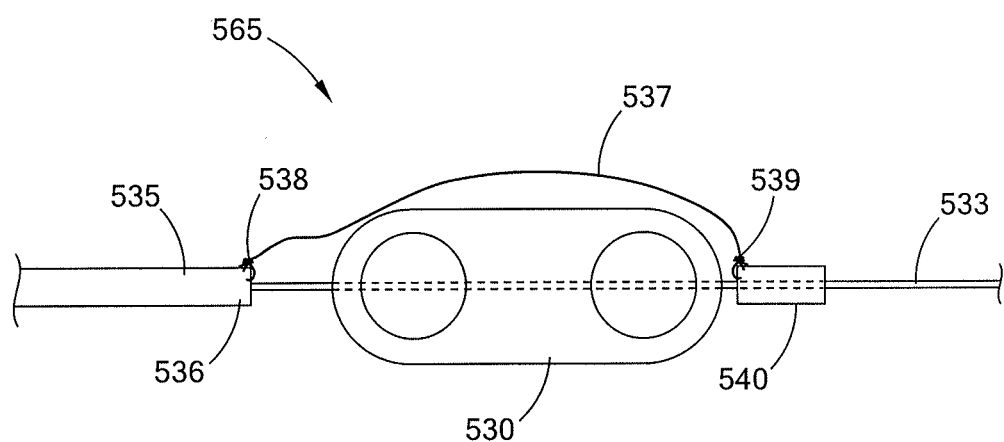
FIG. 15 is a top view of still yet another embodiment of a delivery system constructed in accordance with the teachings of the present invention.

Turning now to FIG. 15, yet another embodiment of a magnet delivery system 565 is shown. In this embodiment the catheter 535 includes a distal end 536 where the strand 537 is fixedly attached thereto. This may be accomplished by tying a first end 538 of the strand to the distal end 536 of the catheter 535 as shown, or it may be attached by welding, bonding, adhesives or other known attachment means. A second end 539 of the strand 537 is fixedly attached to a connector 540 by tying or any of the other above-noted means. The connector 540 is preferably a short tubular member, such as a portion of a catheter, cannula, sheath or the like. As used in describing the connector 540, the term "short" means that the tubular connector 540 has a length substantially shorter (e.g. less than 5 percent) than the length of the catheter 535. As with the prior embodiment, the wire guide 533 may be withdrawn proximally to detach it from the tubular connector 540, and then further retracted to remove it from the lumen of the magnet 530 to deploy the magnet. It will be recognized that in this embodiment, the catheter 535 need only have a single lumen (although the strand and wire guide may share a lumen in the prior embodiments), and the strand 537 is of much shorter length. Preferably the strand 537 has a length that is about one to two times the distance equal to one half of the outer perimeter of the magnet 530.

The foregoing description of has been presented for purposes of illustration and description. It is not intended to be exhaustive or to limit the delivery systems and methods disclosed. Numerous modifications or variations are possible in light of the above teachings. The delivery systems and methods disclosed were chosen and described to provide the best illustration of the principles of the delivery systems and methods and their practical application to thereby enable one of ordinary skill in the art to utilize the delivery systems and methods in various embodiments and with various modifications as are suited to the particular use contemplated. All such modifications and variations are within the scope of the delivery systems and methods as determined by the appended claims when interpreted in accordance with the breadth to which they are fairly, legally, and equitably entitled.

The invention claimed is:

1. A magnet delivery system for forming an anastomosis, the delivery system comprising:
   a wire guide;
   a catheter including a delivery portion for advancement into a visceral space, the delivery portion having a first catheter lumen extending at least partially therethrough and slidably receiving the wire guide, the delivery portion including a distal end of the catheter, wherein the distal end has a terminal end;
   a strand connected to the catheter, a distal end of the strand having a connector slidably connected to the wire guide, the connector selectively detachable from the wire guide; and
   a first magnet defining a lumen therethrough, wherein the first magnet is detachably connected to the delivery portion of the catheter via the wire guide being disposed through the lumen of the first magnet such that a proximal end of the first magnet is positioned adjacent the terminal end of the catheter, the strand extending alongside the first magnet and the connector of the strand slidably connected to the wire guide, wherein neither the strand nor the connector are directly attached to the first magnet.

2. The magnet delivery system of claim 1, wherein the connector includes an aperture sized to slidably receive the wire guide.

3. The magnet delivery system of claim 2, wherein the connector is a loop formed by the strand, the loop defining the aperture.

4. The magnet delivery system of claim 3, wherein the loop is formed by a distal end of the strand being folded over and connected to a distal portion of the strand.

5. The magnet delivery system of claim 3, wherein the loop is formed by the strand being folded over and both ends of the strand extending proximally through the catheter.

6. The magnet delivery system of claim 5, wherein both ends of the strand are accessible at a proximal end of the catheter.

7. The magnet delivery system of claim 1, wherein the connector is slidably attached to the wire guide at a point distal to a distal end of the first magnet, whereby the first magnet is contained between the terminal end of the catheter and the connector.

8. The magnet delivery system of claim 1, wherein the first magnet defines an interior opening between its proximal and distal ends, the interior opening in communication with the lumen, and wherein the connector is slidably attached to the wire guide at a point within the interior opening.

9. The magnet delivery system of claim 1, wherein the strand is slidably connected to the catheter when the first magnet is connected to the delivery portion of the catheter via the wire guide extending through the lumen of the first magnet and the connector being slidably attached to the wire guide.

10. The magnet delivery system of claim 1, wherein the delivery potion of the catheter includes a second catheter lumen extending at least partially therethrough, the second catheter lumen slidably receiving the strand.

11. The magnet delivery system of claim 1, wherein the connector includes a short tube separately formed from the strand.

12. The magnet delivery system of claim 11, wherein the strand is fixedly attached to the terminal end of the catheter, and wherein the strand is fixedly attached to the connector.

13. The magnet delivery system of claim 1, wherein the system is operable between a delivery configuration and a deployed configuration while the first magnet is in vivo, the delivery configuration including the wire guide positioned within the lumen of the first magnet such that a proximal end of the first magnet is positioned adjacent the terminal end of the catheter, and the strand extending alongside the first magnet and the connector slidably attached to the wire guide at a location distal to the proximal end of the first magnet, the deployed configuration including the connector being detached from the wire guide and the wire guide removed from the lumen of the first magnet.

14. The magnet delivery system of claim 1, further comprising a suture lock positioned at a proximal end of the catheter, the suture lock operable to fix the position of the strand portions extending through the suture lock relative to the catheter.

15. The magnet delivery system of claim 14, wherein a proximal portion of the catheter includes a side opening, and wherein the wire guide extends through the side opening and does not extend through the suture lock.

16. The magnet delivery system of claim 15, wherein the catheter includes a second catheter lumen extending at least partially therethrough, the second catheter lumen slidably receiving the strand, and wherein the side opening is in communication with the second catheter lumen and not in communication with the first catheter lumen.

17. The magnet delivery system of claim 1 where the first magnet includes two magnetic members.

18. A magnet delivery system for forming an anastomosis, the delivery system comprising:
a wire guide;
a catheter including a delivery portion for advancement into a visceral space, the delivery portion having a first catheter lumen extending at least partially therethrough and slidably receiving the wire guide, the delivery portion including a distal end of the catheter, wherein the distal end has a terminal end;
a strand connected to the catheter, a distal end of the strand having a connector slidably connected to the wire guide, the connector selectively detachable from the wire guide, wherein a proximal end of the strand fixedly attached to the distal end of the catheter; and
a first magnet defining a lumen therethrough, wherein the first magnet is detachably connected to the delivery portion of the catheter via the wire guide being disposed through the lumen of the first magnet such that a proximal end of the first magnet is positioned adjacent the terminal end of the catheter, and the strand extending alongside the first magnet and the connector of the strand slidably connected to the wire guide, wherein neither the strand nor the connector are directly attached to the first magnet.

19. The magnet delivery system of claim 18, wherein the connector of the strand is slidably connected to the wire guide at a location distal to a distal end of the magnet.

\* \* \* \* \*